United States Patent [19]
Fabricant et al.

[11] Patent Number: 4,578,059
[45] Date of Patent: Mar. 25, 1986

[54] EXTRA-CAPSULAR CATARACT SURGERY SYSTEM

[76] Inventors: Robert N. Fabricant, 285 E. 24th St., Upland, Calif. 91786; Ronald J. Gangemi, 14625 Youbet Rd., Grass Valley, Calif. 94545

[21] Appl. No.: 607,411

[22] Filed: May 7, 1984

[51] Int. Cl.[4] .................. A61M 3/00; A61M 35/00
[52] U.S. Cl. ........................................ 604/43; 604/289
[58] Field of Search .................. 604/43, 45, 93, 289

[56] References Cited

U.S. PATENT DOCUMENTS

| | | | |
|---|---|---|---|
| 3,994,297 | 11/1976 | Kopf | 604/43 |
| 4,014,333 | 3/1977 | McIntyre | 604/43 |

*Primary Examiner*—Mark L. Bell
*Attorney, Agent, or Firm*—Gausewitz, Carr & Rothenberg

[57] ABSTRACT

An extra-capsular cataract surgery system including a handpiece having first and second passageways for irrigation and aspiration purposes, respectively, the system including an attachment for quick connection to the handpiece, the attachment having first and second passages for communication with the passageways of the handpiece, the attachment having a main body portion with a first cannula fixedly attached thereto in an axial position with a piston-like member having a second cannula configured for being received on the first cannula in coaxial sealing relation. Each cannula has a port adjacent the end thereof. The piston-like member is received within a bore in the main body portion and is rotatable and axially displaceable therein. A luer attachment is provided for connection to the handpiece for infusion only.

13 Claims, 5 Drawing Figures

EXTRA-CAPSULAR CATARACT SURGERY SYSTEM

BACKGROUND OF THE INVENTION

The background of the invention will be discussed in two parts:

1. Field of the Invention

This invention relates to systems for use in cataract surgery, and more particularly to a system for use in extracapsular cataract surgery.

2. Description of the Prior Art

In the performance of cataract surgery, an incision is made in the surgical limbus to provide access to the posterior chamber which contains the clouded lens which must be removed. During this surgery, a capsulotomy is performed, that is, incisions are made in the capsule to permit removal of the nucleus using one of several standard techniques.

As the surgery is performed, the surgeon utilizes equipment, tools and instruments such as suction cutters and irrigation and aspiration equipment. One such apparatus for use in this type of surgery is referred to as the McIntyre Coaxial Cannula System, this system including a handpiece with a connector configured for receiving one or more accessories. A first accessory includes separate inner and outer cannulae, mountable coaxially, with the inner needle providing for aspiration, and the passage between the inner and outer needles providing for irrigation.

The handpiece is connectable to first and second tubes, which are, in turn, connectable to infusion and aspiration systems, with appropriate passages within the handpiece suitably interconnecting the source to the appropriate needle. The infusion source usually includes a bottle of a solution, such as a balanced salt solution, connected by means of a suitable needle to the tubing, with the bottle at an elevated position for gravity feed. The aspiration source is usually suction equipment, such as a syringe, with both sources suitably controllable by the surgeon.

In the McIntyre Coaxial Cannula System, the outer cannula terminates in proximate relation to the inner(or longer) cannula, with this relation being fixed, unless other cannula are manually connected or reconnected. With this arrangement, in those instances when irrigation and aspiration are being accomplished simultaneously, close attention must be paid to the irrigation pressure and suction, both of which are occurring in physically proximate relation. For example, after removal of the nucleus, the capsular bag may be filled with cortical material which must be removed to cleanse the capsule for intraocular lens implantation. In such cases, irrigation and aspiration are used simultaneously, with aspiration sometimes accomplished in bursts of application of suction. The irrigation prevents collapse of globe as aspiration is performed.

Another such irrigation/aspiration apparatus is described in an article entitled "Simplified Extracapsular Cataract Extraction" by C. William Simcoe, M.D., published in the American Intra-Ocular implant Society Journal, Volume V, in April of 1979, the article appearing at Pages 154 and 155. In that article, Dr. Simcoe describes the creation of an outer cannula formed of Teflon tubing with an irrigating hole created in the tubing or sleeve by notching the side, the sleeve then being placed over a steel inner cannula or needle. With such devices, although side irrigation is intended, the tubing tends to leak, thus providing irrigation in the direction of the needle, that is, longitudinal.

It is accordingly an object of the present invention to provide a new and improved system for extra-capsular cataract surgery.

It is another object of the present invention to provide a new and improved extra-capsular system.

It is a further object of the present invention to provide a new and improved coaxial cannula system with provision for readily adjusting the spacing between irrigation and aspiration ports, as well as adjusting the direction of irrigation during use.

It is still another object of the present invention to provide a new and improved coaxial cannula system which includes provision for ready connection of other instruments.

SUMMARY OF THE INVENTION

The foregoing and other objects of the invention are accomplished by providing a system including a disposable handpiece configured for ready connection to one or more accessories, such as suction cutters, and irrigation/aspiration devices. The irrigation/aspiration attachment includes a member with a threaded end connectable to the handpiece, the member having a cylindrical bore with a stainless steel cannula extending therefrom. A flexible plastic cannula is secured to a piston-like member insertable within the bore, the Teflon cannula having an inner diameter larger than the outer diameter of the steel cannula, and being shorter in dimension for assembly over the steel cannula in coaxial relation, the so-assembled unit providing an aspiration passage through the center cannula and an irrigation passage through the toroidal opening between the inner and outer cannulae. The outer cannula is configured with a side irrigation port, with the terminal end snugly embracing the inner cannula in sealing relation. The piston-like member is provided with seals and is axially adjustable and rotatable relative to the cylinder or bore of the attachment member.

By sliding the piston member the surgeon is able to selectively separate suction from inflow during removal of the cortical and/or capsular material. The handpiece is connected to two sections of tubing, one of which is connectable to aspiration means such as a syringe, the other of which is connectable to an irrigation system, the latter tubing having an inline bacterial filter. A Luer attachment is provided for connection to the handpiece, the Luer having a single passage for irrigation only.

Other objects, features and advantages of the invention will become apparent from a reading of the specification, when taken in conjunction with the drawings, in which like reference numerals refer to like elements in the several views.

BRIEF DESCRIPTION OF THE DRAWINGS

FIG. 1 is a perspective view depicting the extra-capsular cataract surgery system according to the invention, including attachments and the like;

DESCRIPTION OF THE PREFERRED EMBODIMENT

Figure 1:
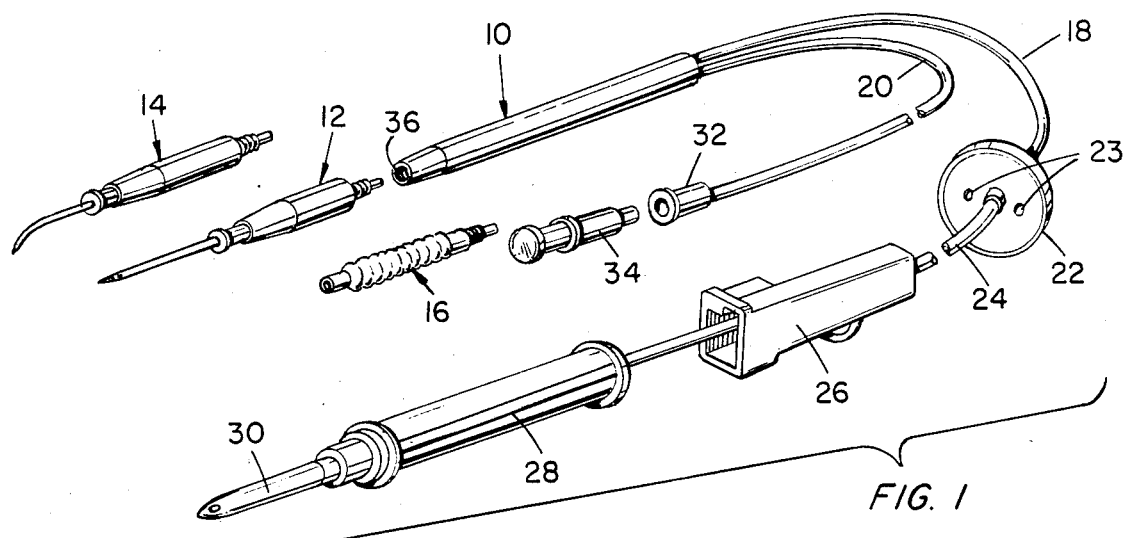

Referring now to the drawings, and particularly to FIG. 1 there is shown an extracapsular cataract surgery system according to the invention, the system including a handpiece 10 to which may be secured attachments such as an irrigation/aspiration device 12, a bent needle suction device 14, or a luer adapter 16 for infusion only.

Two sets of tubing 18 and 20 are connected to the rear of the handpiece, with tubing 18 providing a passage for irrigation fluid, and tubing 20 providing a passage for aspiration. Tubing 20 is provided with an inline bacterial filter 22, which is provide with vent openings 23, the other end of which is connected to other tubing 24 which passes through a suitable clamping member 26 configured for selective constriction of the tubing opening by the surgeon to control the flow of fluid therethrough. The other end of tubing 24 is connected to a dispensing device 28, which includes a cannula 30 for insertion through the rubber stopper of a bottle of irrigation fluid, such as a basic salt solution.

The end of the other set of tubing 20 is connected to a fitting 32, which may be connected to a suitable aspiration system, such as syringe 34. The tubing 18, 20 and 24 is conventional surgical tubing, preferably disposable. The filter 22, as well as the flow clamp 26 and the dispensing device 28 may be of any conventional construction, and do not form a part of the present invention.

In accordance with the present invention, the handpiece 10 is preferably disposable, and is provided at the attachment end with suitable interconnection means, such as a double-threaded female opening 36 configured for receiving any of the attachments 12, 14 and 16. As better illustrated in FIG. 2, the handpiece 10 includes a radially offset axially extending passageway 38 and a central bent passageway 40, with the ends thereof terminating in nipples 39 and 41, respectively, for connection to the tubing 18 and 20, respectively.

Figure 2:
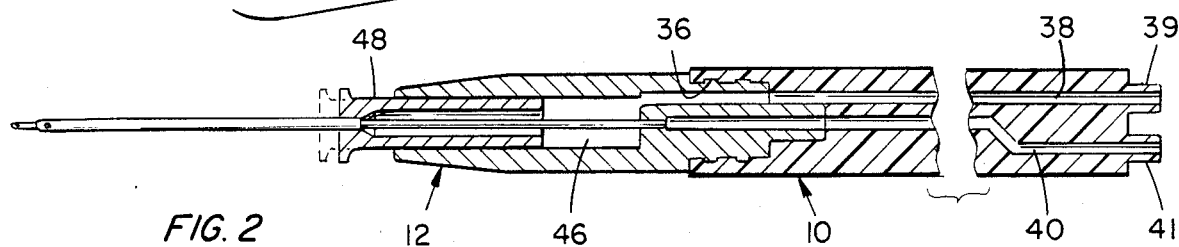
FIG. 2 is a cross-sectional view of the irrigation/aspiration attachment and handpiece used in the system of FIG. 1.
Figure 3:
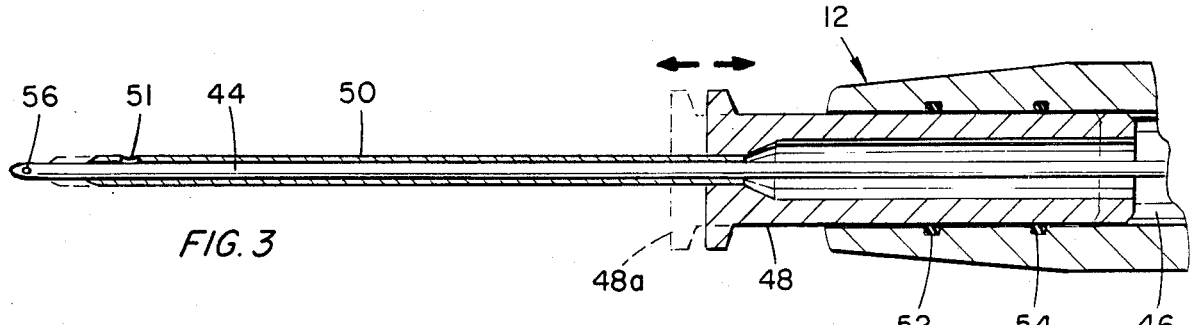
FIG. 3 is an enlarged cross-sectional view of the irrigation/aspiration attachment shown in FIG. 2.

The irrigation/aspiration device 12, by reference to FIGS. 2 and 3, includes a centrally extending stainless steel needle or cannula 44 arranged and configured for communicating with the passageway 40 upon connection to the handpiece 10. The interior chamber of the device 12 is enlarged to form a bore or cylinder 46, into which is inserted a piston-like member 48 having a second cannula 50 attached centrally relative thereto, the cannula 50 having an inner diameter slightly greater than the external diameter of the cannula 44.

The cannula 50 is formed of a flexible material such as Teflon material or the like, and readily conforms to the surface and configuration of the inner cannula 44, and by way of example, the cannula 50 can be used with the bent tip of device 14 for forming a coaxial device.

Figure 4:
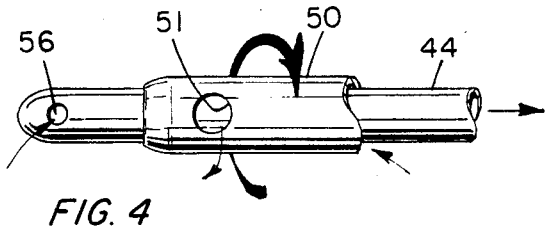
FIG. 4 is an enlarged view of the tip end of the irrigation/aspiration attachment shown in FIGS. 2 and 3.

The cylinder 46 is provided with circumferential grooves adjacent the open end thereof for receiving suitable sealing means such as O-rings 52 and 54, which frictionally abut the periphery of the piston-like member 48 during axial movement thereof. Alternatively, the piston-like member 48 may be circumferentially grooved to have the O-rings 52 and 54 thereon. In either event, as best illustrated in FIGS. 3 and 4, the inner cannula 44 has a radially directed opening 56 adjacent the tip thereof. Similarly the outer cannula 50 has a side or radially directed opening or port 51. The outer cannula 50 is configured for the terminal end thereof adjacent the tip being in snug sealing relation during axial and rotational displacement. The length of the outer cannula 50 is such that with the piston member 48 extended axially outwardly, the tip of the outer cannula 50 is in proximate relation to the opening 56, the tip being shown in dotted lines, with the piston member 48 likewise being shown in dotted lines designated 48a. The solid line positions of the piston member 48 and cannula 50 depict the retracted position with the spacing between the irrigation port or opening 51 and the aspiration port 56 being greater, the irrigation port 51 being in fluid flow relation with the toroidal opening in the space between the outer surface of the cannula 44 and the inner surface of the outer cannula 50.

The device 12 is preferably formed of sterilizable material, such as stainless steel, with the housing of the device 12 and the inner cannula 44 being an integral unit. The pistonlike member 48 and the outer cannula 50 may be formed in separate parts which are then secured to one another, or may be formed as a unitary member from a suitable self-lubricating material such as Teflon.

With the piston member 48 axially slidable and rotatable relative to the housing of the device 12, the surgeon has the capability of separating the irrigation port 51 from the aspiration port 56 during use, thus facilitating removal of debris from within the wound. In addition with the rotational ability of the piston-like member 48, the surgeon, during use, may selectively direct the irrigation to readily remove debris.

Figure 5:
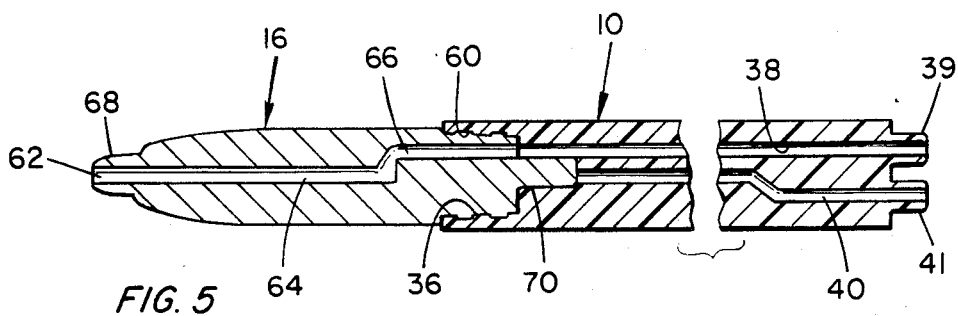
FIG. 5 is a cross-sectional view of the luer attachment connected to the handpiece of the sytem of FIG. 1.

Referring now to FIG. 5, the attachment 16 is depicted in cross-sectional view, the attachment 16 having a double-threaded end 36 for mounting to the mating opening 36 of the handpiece 10. The tip 68 of the attachment 16 has an opening 62 which communicates with a passageway 64 which is offset at 66 to align with the passageway 38 of the handpiece 10, this passageway being for irrigation purposes. The end of the attachment 16 opposite the tip 68 is provided with a centrally positioned stub fitting 70 which abuts the opening of the aspiration passageway 40 to seal the same, thus providing an attachment for irrigation purposes only. The tip 68 is suitably configured as a male Luer fitting for ready attachment of other instruments, such as needles or other instruments which may be used for irrigation or flushing only.

In accordance with the invention, the system includes a handpiece 10, which may be disposable along with the tubing 18 and 20, the filter 22, the flow clamp 26, and the dispenser device 28. With the opening 36 of the handpiece 10 having a female double-threaded configuration, any of the attachments 12, 14 and 16 may be quickly attached. By providing axial adjustment as well as rotational adjustment capability of the coaxial cannulae 44 and 50, selective spatial separation of the irrigation and aspiration ports may be accomplished, with direction of irrigation under the control of the surgeon. While there has been shown and described a preferred embodiment of the extra-capsular cataract surgery system according to the invention, other adaptations and modifications may be made within the spirit and scope of the invention.

We claim:

1. In a system for use in extra-capsular cataract surgery, the combination comprising:

a handpiece having first and second longitudinally extending passageways for aspiration and irrigation purposes;

a device attachable to said handpiece in axial alignment therewith, said device having a main body portion with a bore therein and having a first generally rigid cannula secured thereto generally centrally relative to said bore for providing a first flow passage for communication with said first passageway of said handpiece, said first cannula having first port means adjacent the tip thereof; and a piston member rotatably and slidably assembled within said bore on said main body portion, said piston member having a second generally flexible cannula secured thereto in an axial direction, said second cannula being configured for being assembled on said first cannula with the terminal end of said second cannula being in generally sealing relation, said second cannula having port means adjacent the terminal and thereof, said member and said second cannula being in flow communication with said second passageway means within said device whereby the port means of said second cannula may be displaced axially and circumferentially relative to said port means of said first cannula during use thereof.

2. The combination according to claim 1 wherein said first cannula means is a needle formed of a steel composition.

3. The combination according to claim 1 wherein said port means of said first cannula means is radially directed.

4. In a device for attachment to a handpiece of a system used in extra-capsular cataract surgery, the handpiece having first and second passageways for aspiration and irrigation purposes respectively, the combination comprising:

a main body portion having a bore with first and second passages therein for communicating with said first and second passageways;

a cannula member secured to said main body portion in axial alignment with said bore, the interior of said cannula being in flow communication with said first passage and having a port adjacent the tip thereof;

a piston member rotatably and slidably assembled within said bore of said main body portion, said piston member having secured thereto a second flexible tubular cannula of shorter dimension than said first cannula in coaxial relation therewith and having the terminal end thereof in sealing relation with said first cannula, said second cannula being in flow communication with said second passage and having a port adjacent the terminal end thereof, whereby manipulation of said piston member during use by the surgeon axially and rotationally displaces the port of said second cannula relative to the port of said first cannula.

5. The combination according to claim 4 wherein said combination further includes means on said piston-like member for providing sealing during the sliding and rotational movement of said piston-like member.

6. The combination according to claim 5 wherein said first cannula is a steel needle having a side facing port adjacent the tip thereof.

7. The combination according to claim 6 wherein said second cannula is formed of a Teflon composition material.

8. In a system for use in extra-capsular cataract surgery, the combination comprising:

a handpiece having first and second passageways formed therein;

means for attaching said handpiece to other means for providing aspiration and irrigation functions through said first and second passageways;

an axially extending threaded opening formed in said handpiece for attaching one of at least a first and second device, each of said devices having a threaded mating end for being received within said opening; said first device including:

a main body portion having a bore with first and second flow passages configured for flow relation with said first and second passageways;

a first cannula secured to said main body portion in axial alignment with said bore and extending therefrom with said first cannula in flow relation with said first flow passage, said first cannula having a port adjacent the tip thereof;

a piston member within said bore of said main body portion and having a second generally flexible cannula in coaxial relation with said first cannula, said second cannula having a length less than the length of said first cannula and having the terminal end thereof in sealing relation with said first cannula, said second cannula having a port adjacent the terminal end thereof, said piston member being in slidable and rotatable relation relative to said main body portion; and said second device having a single passage therethrough for fluid communication only with said second passage of said handpiece.

9. The combination according to claim 1 wherein said first cannula is an arcuately configured cannula formed of a metallic composition.

10. The combination according to claim 1 wherein said handpiece includes a threaded opening in one end thereof and said device includes a matingly threaded end for attachment thereto.

11. The combination according to claim 4 wherein said first cannula is an arcuately configured cannula formed of a metallic composition.

12. The combination according to claim 11 wherein said handpiece includes a threaded opening in one end thereof and said device includes a matingly threaded end for attachment thereto.

13. The combination according to claim 8 wherein said first cannula is an arcuately configured cannula formed of a metallic composition.

* * * * *